United States Patent
Jung et al.

(10) Patent No.: US 9,919,932 B2
(45) Date of Patent: Mar. 20, 2018

(54) NICKEL FERRITE NANOPARTICLE COMPOSITE AND METHOD FOR PREPARING SAME

(75) Inventors: Gyoo Yeol Jung, Pohang-si (KR); Sang Woo Seo, Seoul (KR); Jinyoung Chun, Anyang-si (KR); Jinwoo Lee, Seoul (KR)

(73) Assignee: POSTECH ACADEMY-INDUSTRY FOUNDATION, Pohang-si, Gyeongsangbuk-Do (KR)

( * ) Notice: Subject to any disclaimer, the term of this patent is extended or adjusted under 35 U.S.C. 154(b) by 752 days.

(21) Appl. No.: 14/240,277

(22) PCT Filed: Mar. 29, 2012

(86) PCT No.: PCT/KR2012/002341
§ 371 (c)(1),
(2), (4) Date: Feb. 21, 2014

(87) PCT Pub. No.: WO2013/027909
PCT Pub. Date: Feb. 28, 2013

(65) Prior Publication Data
US 2014/0163209 A1    Jun. 12, 2014

(30) Foreign Application Priority Data
Aug. 23, 2011 (KR) ........................ 10-2011-0083833

(51) Int. Cl.
| | | |
|---|---|---|
| *C01G 53/04* | (2006.01) | |
| *C07K 1/14* | (2006.01) | |
| *C07K 1/22* | (2006.01) | |
| *C01G 53/00* | (2006.01) | |
| *H01F 1/00* | (2006.01) | |
| *H01F 1/36* | (2006.01) | |
| *B82Y 30/00* | (2011.01) | |

(52) U.S. Cl.
CPC ............ *C01G 53/04* (2013.01); *C01G 53/40* (2013.01); *C07K 1/14* (2013.01); *C07K 1/22* (2013.01); *H01F 1/0054* (2013.01); *B82Y 30/00* (2013.01); *C01P 2002/72* (2013.01); *C01P 2002/85* (2013.01); *C01P 2004/03* (2013.01); *C01P 2004/04* (2013.01); *C01P 2004/64* (2013.01); *C01P 2006/12* (2013.01); *C01P 2006/14* (2013.01); *C01P 2006/17* (2013.01); *C01P 2006/42* (2013.01); *H01F 1/36* (2013.01); *Y10T 428/2982* (2015.01)

(58) Field of Classification Search
CPC ........ B82Y 30/00; C01G 53/04; C01G 53/40; C01P 2002/72; C01P 2002/85; C01P 2004/03; C01P 2004/04; C01P 2004/64; C01P 2006/12; C01P 2006/14; C01P 2006/17; C01P 2006/42; C07K 1/14; C07K 1/22; H01F 1/0054; H01F 1/36
See application file for complete search history.

(56) References Cited

U.S. PATENT DOCUMENTS

2008/0003159 A1* 1/2008 Cheon ................... B82Y 25/00
                                                            423/263

FOREIGN PATENT DOCUMENTS

| KR | 10-0604975 B1 | 5/2006 |
| KR | 10-2008-0055485 A | 6/2008 |

OTHER PUBLICATIONS

Šepelák et al., "Nanocrystalline Nickel Ferrite, NiFe2O4: Mechanosynthesis, Nonequilibrium Cation Distribution, Canted Spin Arrangement, and Magnetic Behavior," J. Phys. Chem. C, 2007, vol. 111, No. 13, pp. 5026-5033.*
Chkoundali et al., "Nickel ferrite nanoparticles: elaboration in polyol medium via hydrolysis, and magnetic properties," J. Phys.: Condens. Matter, 2004, vol. 16, pp. 4357-4372.*
Tamura et al., "Precipitation of Cobalt Ferrites," J. Colloid Interface Sci., 1982, vol. 90, No. 1, pp. 100-109.*
C. Xu et al; Nitrilotriacetic acid-modified magnetic nanoparticles as a general agent to bind . . . ; J. Am. Chem. Soc. 2004, vol. 126, pp. 3392-3393.
C. Xu et al; Dopamine as a robust anchor to immobilize functional molecules on the iron oxide shell . . . ; J. Am. Chem. Soc. 2004, vol. 126, pp. 9938-9939.
K.B. Lee et al; Multicomponent magnetic nanorods for biomolecular separations; Angew. Chem. Int. Ed. 2004, vol. 43, pp. 3048-3050.
B.K. Oh et al; Separation of tricomponent protein mixtures with triblock nanorods; J. Am. Chem. Soc. 2006, vol. 128, pp. 11825-11829.
S. Lee et al; Ni/NiO Core/Shell nanoparticles for selective binding and magnetic separation of histidine-tagged proteins; J. Am. Chem. Soc. 2006, vol. 128, pp. 10658-10659.
J. Chun et al; Easy access to efficient magnetically recyclable separation of histidine-tagged proteins . . . ; J. Mater. Chem.; Mar. 30, 2011; vol. 21; pp. 6713-6717.
J. Wang et al; Solvothermal synthesis and magnetic properties of size-controlled nickel . . . ; J. Alloys Compds., 2009, vol. 479; pp. 791-796.

(Continued)

Primary Examiner — Galina Yakovleva
(74) Attorney, Agent, or Firm — Lucas & Mercanti, LLP

(57) ABSTRACT

The present invention relates to a method for preparing a nickel ferrite nanoparticle composite having an inverse spinel structure obtained using a polyol process, a nickel ferrite nanoparticle composite prepared by the method, and a method for selectively binding, separating or purifying a specific protein using the nickel ferrite nanoparticle composite. The method for preparing a magnetic nanoparticle composite according to the present invention includes a one-step hydrothermal synthesis process, and thereby the magnetic nanoparticle composite can be prepared in a simple and economic manner. Also, the nickel ferrite nanoparticles synthesized by the method of the present invention can be strongly magnetic, and also exist in the form of $Ni^{2+}$ in which Ni binds to a specific protein, thereby preventing loss of separability caused by additional oxidation and repeated recycling of the nanoparticles.

4 Claims, 7 Drawing Sheets

(56) References Cited

OTHER PUBLICATIONS

J. Chun et al; The magnetic separation of the histidine-tagged protein . . . ; Theories and Applications of Chem. Eng., 2010, vol. 16, No. 2, pp. 2039.
International Search Report dated Oct. 18, 2012.
Deng et al., "Monodisperse Magnetic Single-Crystal Ferrite Microspheres",Angew. Chem. Int. Ed, 2005, vol. 44, pp. 2782-2785.
Cheng et al., "One-step synthesis of superparamagnetic monodisperse porous Fe3O4 hollow and core-shell spheres", J. Mater. Chem, 2010, vol. 20, pp. 1799-1805.

\* cited by examiner

[Fig. 1]
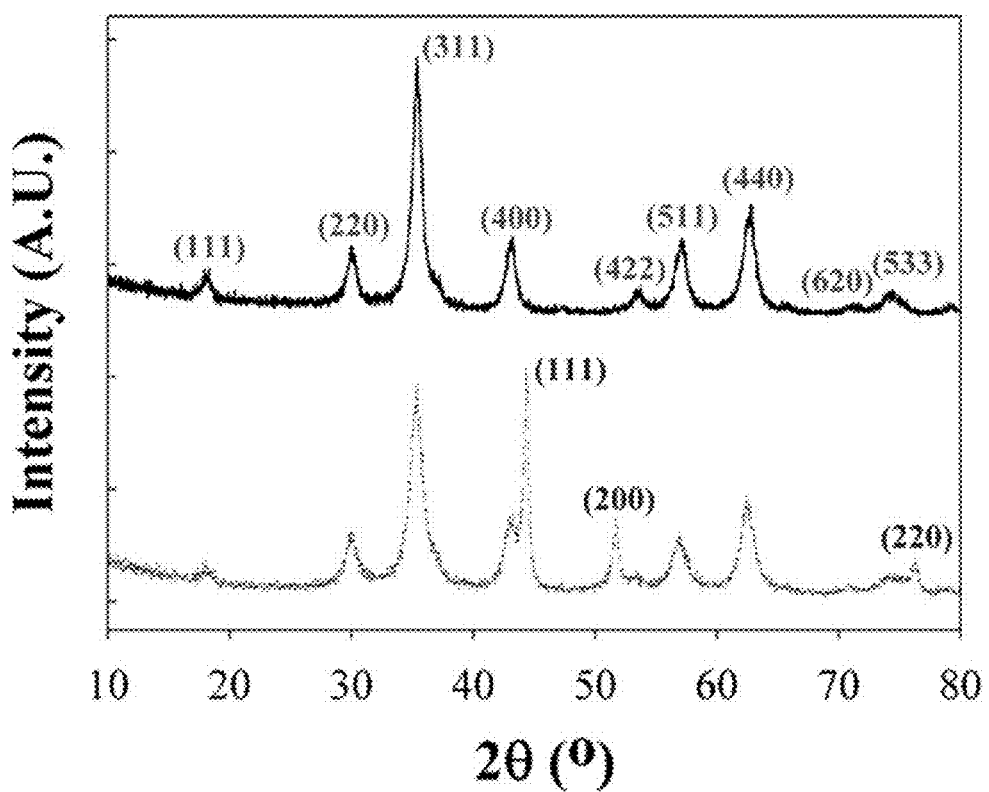
[Fig. 2]
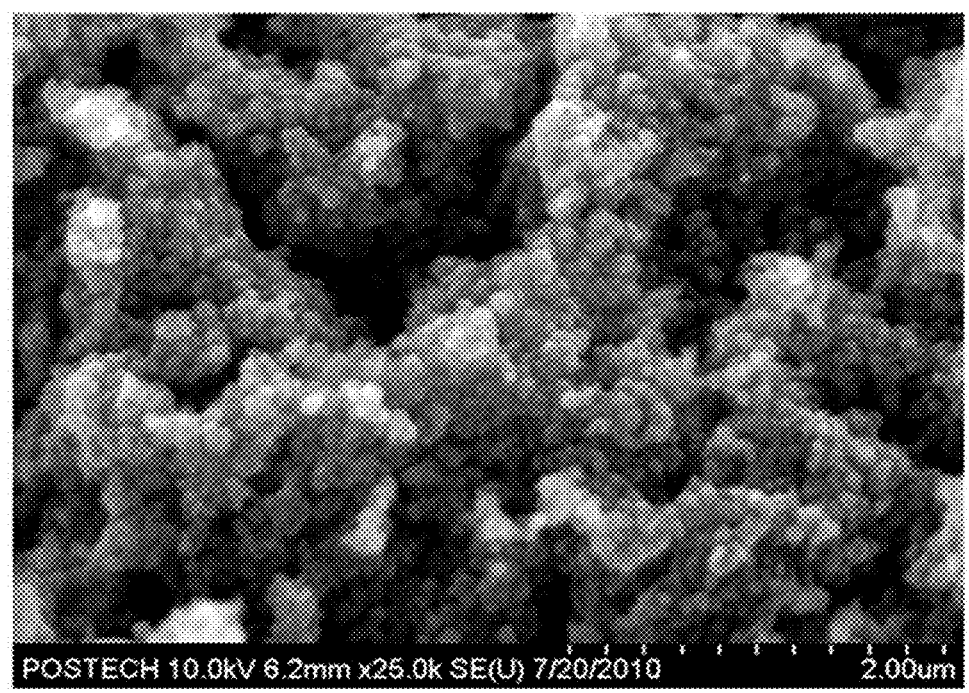

[Fig. 3]
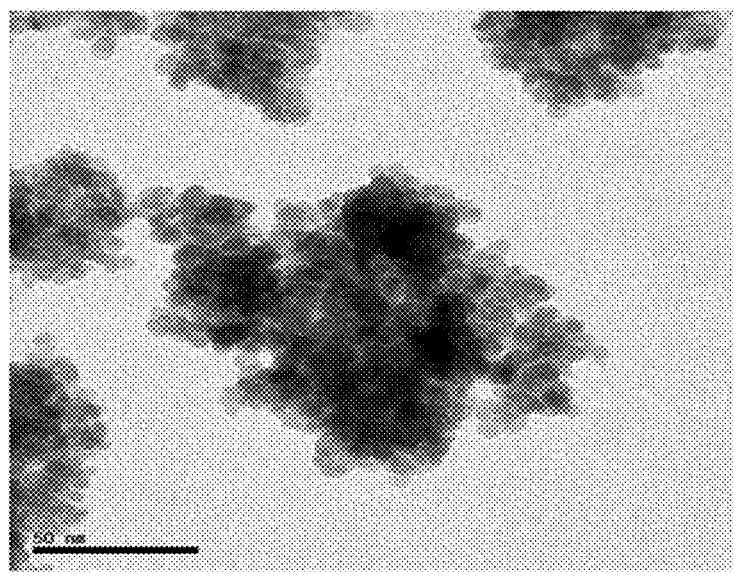
[Fig. 4]
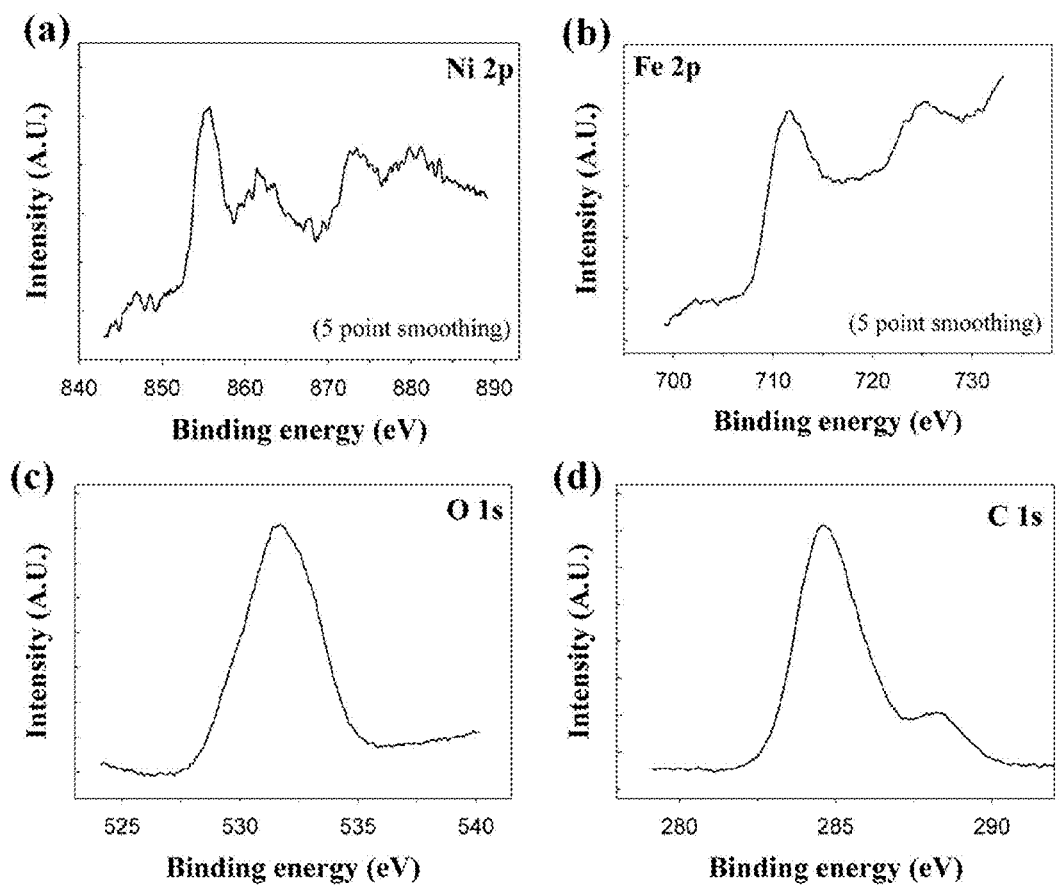

[Fig. 5]
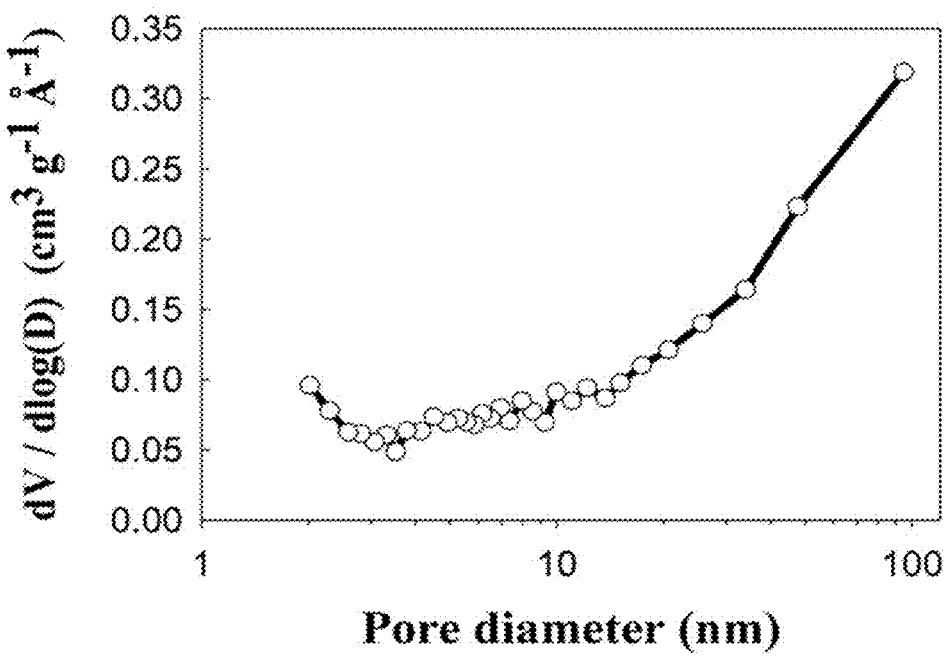
[Fig. 6]
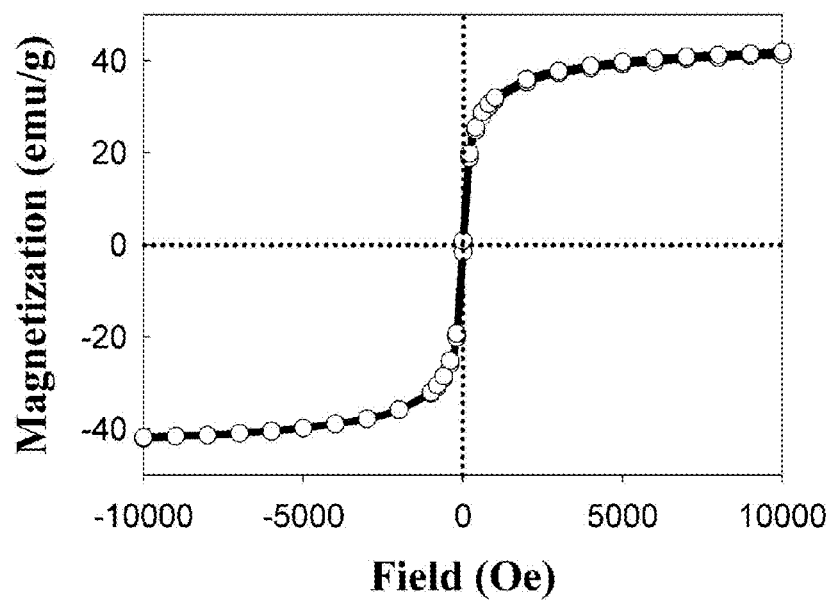

[Fig. 7]
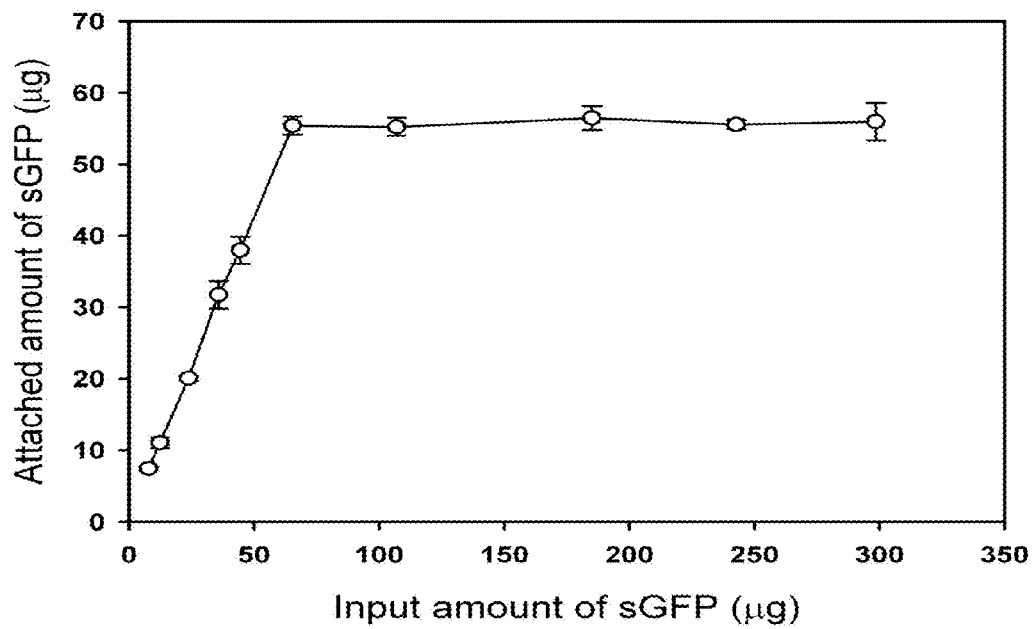
[Fig 8]
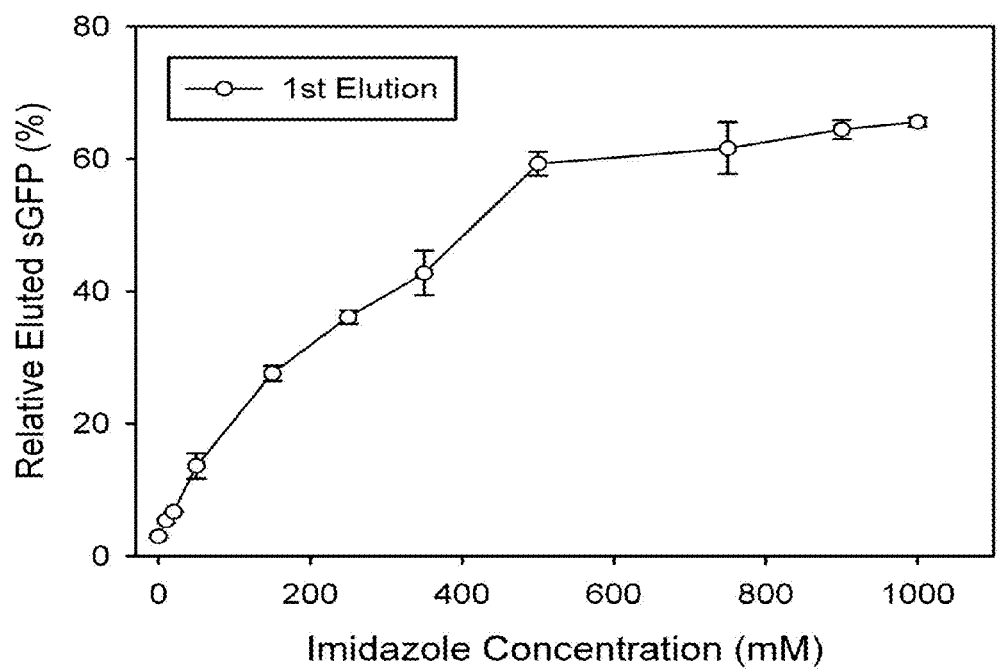

[Fig. 9]
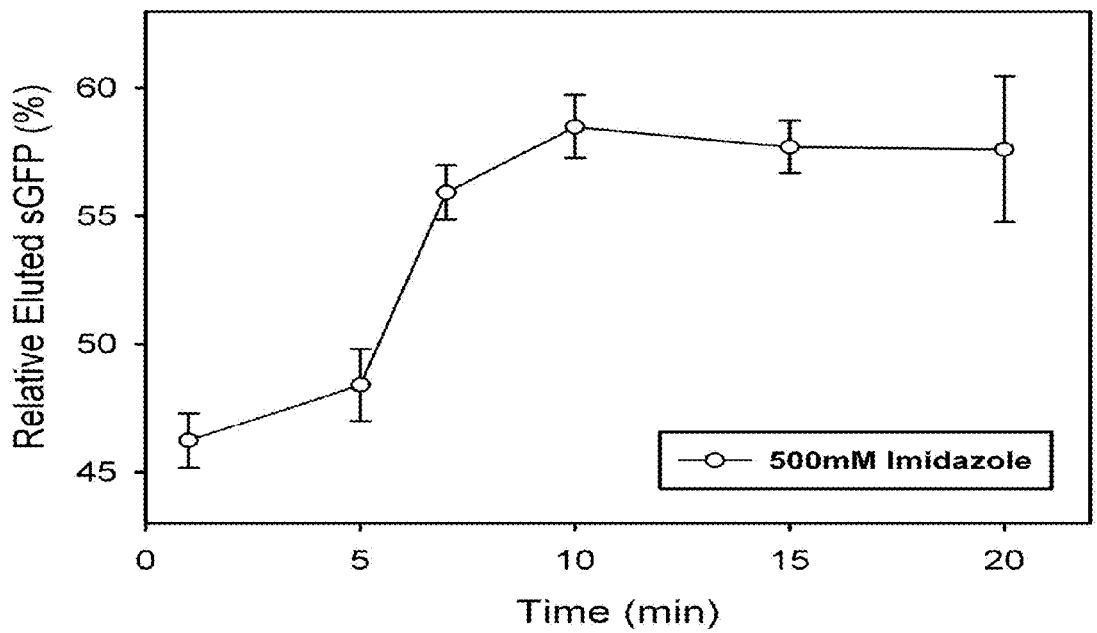
[Fig. 10]
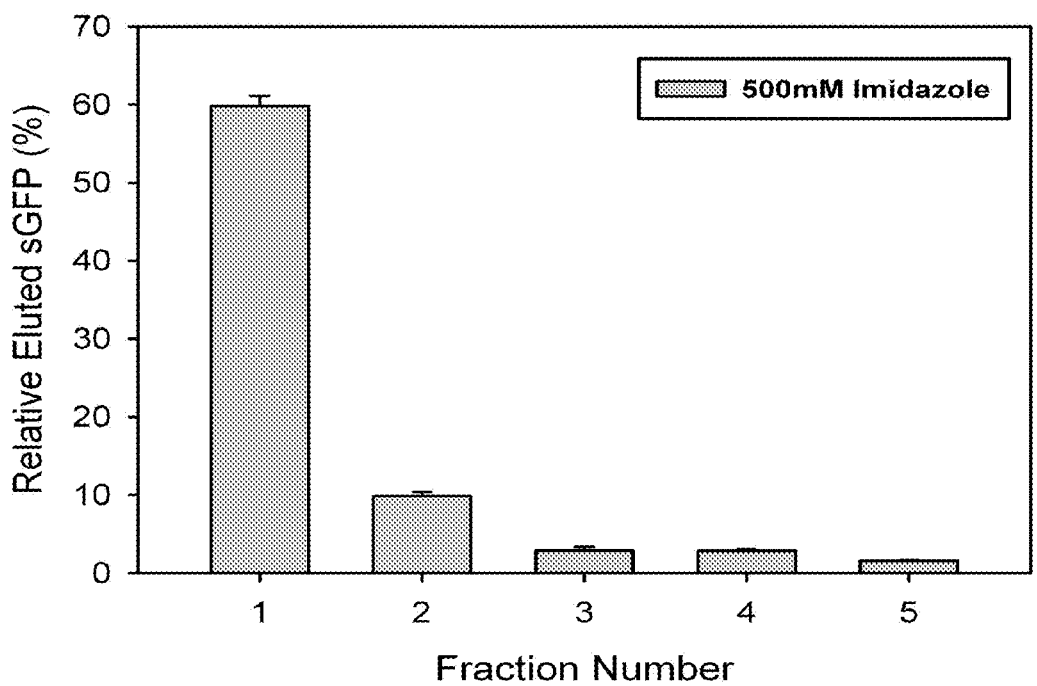

[Fig. 11]
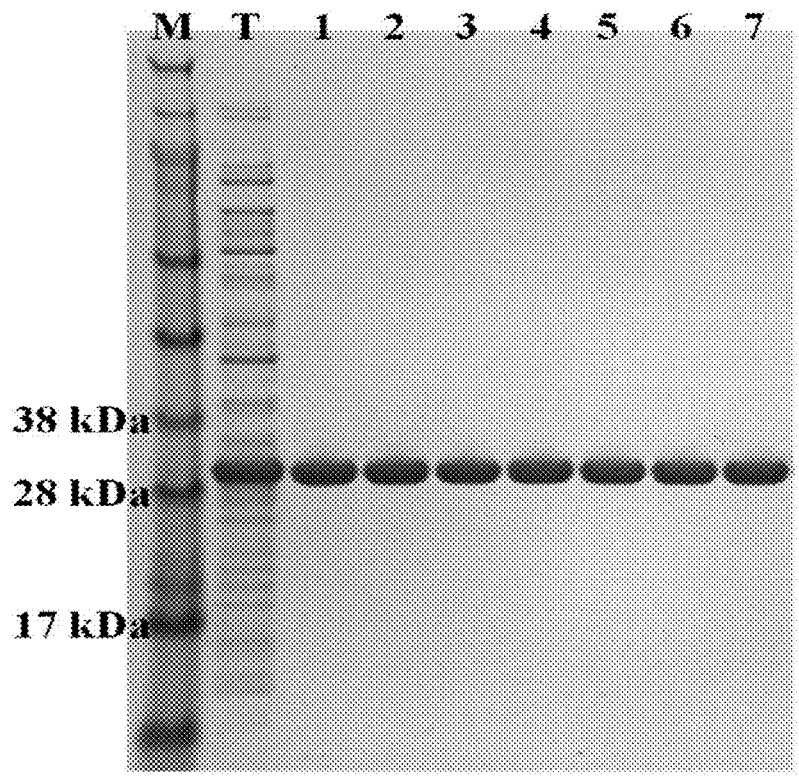
[Fig. 12]
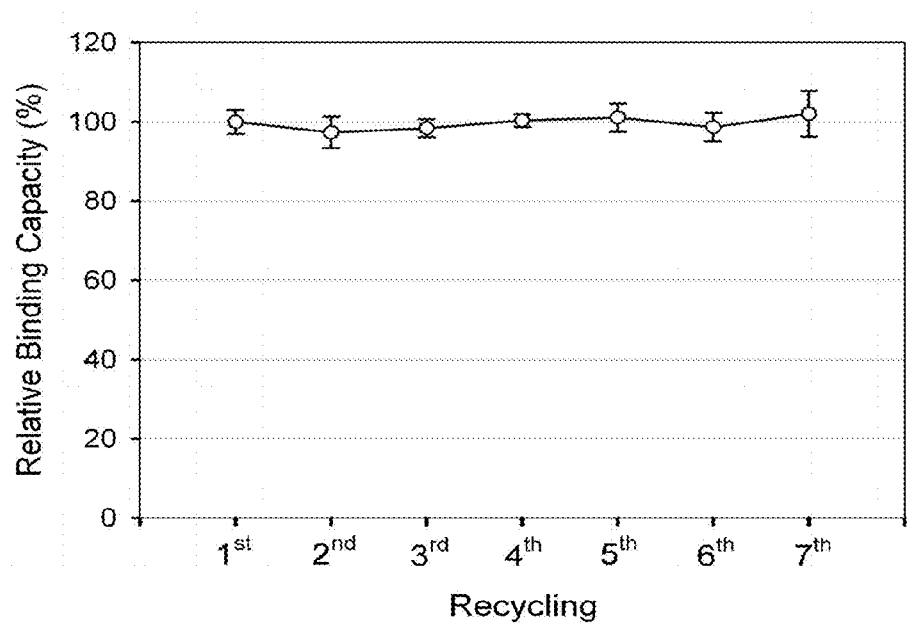

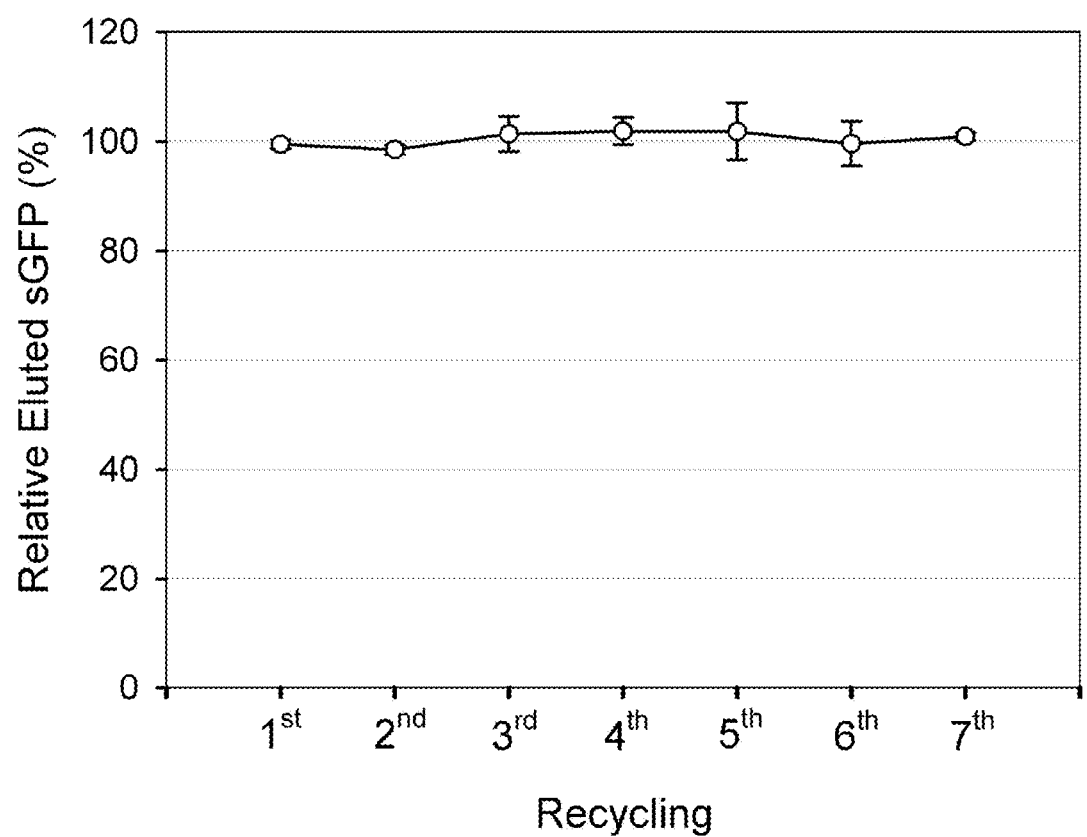
[Fig. 13]

NICKEL FERRITE NANOPARTICLE COMPOSITE AND METHOD FOR PREPARING SAME

CROSS-REFERENCE TO RELATED APPLICATIONS

This application is a 371 of PCT/KR2012/002341, filed Mar. 29, 2012, which claims the benefit of Korean Patent Application No. 10-2011-0083833, filed Aug. 23, 2011, the contents of each of which are incorporated herein by reference.

TECHNICAL FIELD

The present invention relates to a method for preparing a nickel ferrite nanoparticle composite having an inverse spinel structure obtained using a polyol process, a nickel ferrite nanoparticle composite prepared by the method, and a method for selectively binding, separating or purifying a specific protein using the nickel ferrite nanoparticle composite.

BACKGROUND ART

In proteomics, a very important technique is to easily separate and handle a recombinant protein.

Nickel nitrilotriacetic acid (Ni-NTA) beads most frequently used to separate a recombinant protein have been most widely used to purify a protein with an oligohistidine affinity tag (His-tag). A NTA-attached resin is used to fix Ni ions in the Ni-NTA beads and separate a His-tagged protein through coordination chemistry.

In recent years, Xu et al. have synthesized an NTA-attached FePt nanoparticles and an NTA-attached $Co/Fe_2O_3$ magnetic nanoparticles and demonstrated the separation of a His-tagged protein by using the magnetic nanoparticles (C. Xu, K. Xu, H. Gu, X. Zhong, Z. Guo, R. Zheng, X. Zhang, B. Xu, J. Am. Chem. Soc. 2004, 126, 3392; C. Xu, K. Xu, H. Gu, R. Zheng, H. Liu, X. Zhang, Z. Guo, B. Xu, J. Am. Chem. Soc. 2004, 126, 9938).

Mirkin et al. have manufactured an Au—Ni—Au triblock nanorod using an anodic alumina membrane and applied it to magnetic separation of a His-tagged protein (K.-B. Lee, S. Park, C. A. Mirkin, Angew. Chem. 2004, 116, 3110; Angew. Chem. Int. Ed. 2004, 43, 3048; B.-K. Oh, S. Park, J. E. Millstone, S. W. Lee, K.-B. Lee, C. A. Mirkin, J. Am. Chem. Soc. 2006, 128, 11825).

However, in the methods published by Xu et al. and Mirkin et al., the nanoparticles for separating a protein are prepared through a series of complicated organic reaction processes.

In more recent years, Hyeon et al. have disclosed Ni/NiO core/shell nanoparticles for selectively binding and magnetically separating a His-tagged protein (I. S. Lee, N. Lee, J. Park, B. H. Kim, Y.-W. Yi, T. Kim, T. K. Kim, I. H. Lee, S. R. Paik, T. Hyeon, J. Am. Chem. Soc. 2006, 128, 10658).

However, the conventional systems have a problem in that the Ni/NiO nanoparticles should undergo a complicated multi-step organic synthesis process since Ni ions binding to a protein are introduced into surfaces of magnetic particles and a shell is formed around a core showing magnetism using silica or a polymer resin to connect a ligand. Also, when the Ni/NiO nanoparticles are recycled several times, the magnetic Ni core is gradually oxidized into NiO which is a semi-ferromagnetic substance. As a result, it is difficult to recycle the Ni/NiO nanoparticles as the magnetism of the Ni/NiO core/shell nanoparticles gradually decreases.

Meanwhile, a conventional method for preparing a ferrite powder includes mixing a metal oxide and drying, calcining and grinding the resulting mixture to prepare particles. However, the process should be performed at a calcination temperature of 1,200° C. or higher since an oxide is used as a starting material, and requires a long grinding process since compositions and particle size of the particles are not uniformly formed due to a solid-state reaction between the particles, which leads to degraded purity and magnetic characteristics caused by contamination.

In addition to the above-described method, methods for preparing a ferrite, such as coprecipitation, hydrothermal synthesis and a flux method, have been used. However, all the methods have problems in that it is difficult to mass-produce nanoparticles since an apparatus has a complicated configuration and is a batch-type apparatus, a manufacturing time is long, the nanoparticles do not exist as a composite since a new phase is formed by a reaction between raw materials, especially upon manufacture of nanocomposite powder, and it is difficult to obtain a powder having a uniform composition.

DISCLOSURE

Technical Problem

The present invention is designed to solve the problems of the prior art, and therefore it is an object of the present invention to provide a method for preparing a nickel ferrite nanoparticle composite having a novel structure in which nickel ion particles are mixed with a ferrite showing magnetism during a process of preparing magnetic nanoparticles without performing a separate process to introduce nickel ions in order to separate a protein, thereby forming an entire compound structure, and a nickel ferrite nanoparticle composite prepared by the method.

Also, it is another object of the present invention to provide a protein binder including the nickel ferrite nanoparticle composite, and a method for separating and purifying a protein using the protein binder.

However, the problems to be solved according to the present invention are not limited to the above-described problems, and other problems which are not disclosed herein will be made apparent to those skilled in the art from the detailed description provided below.

Technical Solution

According to an aspect of the present invention, there is provided a method for preparing a nickel ferrite nanoparticle composite having an inverse spinel structure. Here, the method includes (1) preparing a mixed solution in which a nickel precursor compound and an iron precursor compound are mixed with a polyol solvent, (2) adding a pH control agent, (3) adding a $Ni^{2+}$ oxidizing agent and agitating the resulting mixed solution, and (4) heating the resulting mixed solution to form a nanoparticle composite through reduction of a nickel salt and an iron salt.

According to one exemplary embodiment of the present invention, in the polyol solvent, one selected from the group consisting of ethylene glycol (EG), diethylene glycol (DEG), triethylene glycol (TEG), tetraethylene glycol (TTEG), and tetratethylene glycol (TtEg) may be used.

According to another exemplary embodiment of the present invention, the pH control agent may be an acetate compound, and, more particularly, sodium acetate.

According to still another exemplary embodiment of the present invention, the $Ni^{2+}$ oxidizing agent may be $KNO_3$, or $NaNO_3$, and may be added at an amount of 0.1 g or more per 1 mL of the resulting mixed solution. Preferably, the $Ni^{2+}$ oxidizing agent may be added at an amount of 0.1 to 0.2 g.

According to still another exemplary embodiment of the present invention, a time required to maintain a reaction temperature of 200° C. or higher may be greater than or equal to 8 hours in the heating of the resulting mixed solution to form the nanoparticle composite.

According to still another exemplary embodiment of the present invention, the method of the present invention may include washing the reacted nanoparticle composite with a washing solvent and drying the nanoparticle composite in a temperature condition ranging from room temperature to 70° C.

According to yet another exemplary embodiment of the present invention, the washing solvent may be at least one selected from the group consisting of ethanol, acetone, and water.

According to another aspect of the present invention, there is provided a nickel ferrite nanoparticle composite prepared by the method for preparing a nickel ferrite nanoparticle composite, in which $Ni^{2+}$ and $Fe^{3+}$ form an inverse spinel structure.

According to one exemplary embodiment of the present invention, the nickel ferrite nanoparticle composite may have a magnetic saturation value of 40 to 50 emu/g.

According to another exemplary embodiment of the present invention, the nickel ferrite nanoparticles may have a particle size of 7 to 10 nm, and the nickel ferrite nanoparticle composite may have a particle size of 80 to 200 nm.

According to still another aspect of the present invention, there is provided a protein binder which includes the nickel ferrite nanoparticle composite having an inverse spinel structure, and has properties of selectively binding to a protein comprising an amino acid selected from the group consisting of histidine, asparagine, arginine, cystine, glutamine, lysine, methionine, proline, and tryptophan.

According to one exemplary embodiment of the present invention, the protein binder may be recycled.

According to yet another aspect of the present invention, there is provided a method for selectively binding, separating or purifying a specific protein, which includes (1) allowing a protein binder including the nickel ferrite nanoparticle composite to bind to a specific protein included in a biological mixture, (2) separating the specific protein bound to the protein binder from the biological mixture using a magnetic field applied from the outside, and (3) separating the separated specific protein from the nickel ferrite nanoparticle composite.

According to one exemplary embodiment of the present invention, the protein may be a protein including at least one amino acid selected from the group consisting of histidine, asparagine, arginine, cystine, glutamine, lysine, methionine, proline, and tryptophan.

Advantageous Effects

As described above, the method for preparing a magnetic nanoparticle composite according to the present invention includes a one-step hydrothermal synthesis method, and thereby the magnetic nanoparticle composite can be prepared in a simple and economic manner. Also, the nickel ferrite nanoparticles synthesized by the method of the present invention can be strongly magnetic, and also exist in the form of $Ni^{2+}$ in which Ni binds to a specific protein, thereby preventing loss of separability caused by additional oxidation and repeatedly recycling the nanoparticles.

DESCRIPTION OF DRAWINGS

These and other features, aspects, and advantages of preferred embodiments of the present invention will be more fully described in the following detailed description, taken accompanying drawings. In the drawings:

FIG. 1 is a diagram showing the X-ray diffraction (XRD) measurement results of structures of magnetic nanocomposites prepared in Example 1 and Comparative Example 1 to compare the structures of the magnetic nanocomposites;

FIG. 2 is a diagram showing the scanning electron microscope (SEM) analysis results of the magnetic nanocomposite prepared in Example 1;

FIG. 3 is a diagram showing the transmission electron microscopy (TEM) analysis results of the magnetic nanocomposite prepared in Example 1;

FIG. 4 is a diagram showing the results obtained by measuring the spectra of target metal oxides according to binding energy of the target metal oxides using X-ray photoelectron spectroscopy (XPS);

FIG. 5 is a diagram showing a pore size distribution curve obtained from the analysis of adsorption results on the magnetic nanocomposite according to one exemplary embodiment of the present invention using a Barett-Joyner-Halenda (BJH) method;

FIG. 6 is a diagram showing the results obtained by investigating magnetic behaviors of the magnetic nanocomposite using a superconducting quantum interference device (SQUID);

FIG. 7 is a diagram showing the results obtained by measuring separability of a His-tagged green fluorescent protein (GFP) according to an amount of the added GFP;

FIG. 8 is a diagram showing a level of separation of a His-tagged GFP according to a concentration of imidazole;

FIG. 9 is a diagram showing a level of separation of a His-tagged GFP according to a reaction time of imidazole;

FIG. 10 is a diagram showing the results obtained by measuring a level of separation of imidazole according to the number of reactions with imidazole;

FIG. 11 is a diagram showing the results obtained by analyzing selective protein separability of the magnetic nanocomposite using SDS-PAGE;

FIGS. 12 and 13 are diagrams showing separation efficiency of a protein according to the number of experiments designed to separate the protein.

BEST MODE

According to the present invention, a nickel ferrite nanoparticle composite having an inverse spinel structure obtained using a polyol process is prepared. A polyol refers to a substance having at least two —OH groups in its molecules, and the polyol process is a method in which a nanosized metal or metal oxide can be uniformly synthesized, and a reaction occurs at a lower temperature than a solid-state method or heat treatment under a reducing hydrogen gas atmosphere since the reaction is performed in a solution, thereby synthesizing the nanosized metal or metal oxide more effectively.

The method for preparing a nickel ferrite nanoparticle composite according to the present invention includes (1) preparing a mixed solution in which a nickel precursor compound and an iron precursor compound are mixed with a polyol solvent, (2) adding a pH control agent, (3) adding a $Ni^{2+}$ oxidizing agent and agitating the resulting mixed solution, and (4) heating the resulting mixed solution to form a nanoparticle composite through reduction of a nickel salt and an iron salt.

The nickel precursor and the iron precursor are salt compounds including nickel and iron. In this case, a nitrate-based compound, a sulfate-based compound, an acetylacetonate-based compound, a fluoroacetoacetate-based compound, a metal halide-based compound, a metal perchlorate-based compound, a metal alkyloxide-based compound, a metal sulfamate-based compound, a metal stearate-based compound, a metal alkoxide-based compound, or an organic metal-based compound may be used as the nickel precursor and the iron precursor, but the present invention is not limited thereto. Also, the nickel precursor and the iron precursor may be mixed at various mixing ratios. Preferably, $NiFe_2O_4$ may be effectively prepared by mixing the nickel precursor and the iron precursor at a mixing ratio of 1:2. When one of the nickel precursor and the iron precursor has a higher mixing ratio, necessary substances such as NiO (which is not easily separated due to its lack of magnetism) or $Fe_3O_4$ (which is not capable of separating proteins) may be synthesized.

Ethylene glycol (EG), diethylene glycol (DEG), triethylene glycol (TEG), tetraethylene glycol (TTEG), and tetratethylene glycol (TtEg) may be used in the polyol solvent.

The pH control agent serves to facilitate a precipitation reaction by controlling pH of a solution of the nickel precursor compound and the iron precursor compound. Here, the pH control agent may be an acetate compound such as sodium acetate.

The present invention is characterized in that, after the nanoparticles are formed as described above, a $Ni^{2+}$ oxidizing agent is added to the nanoparticles to form a composite while $Ni^{2+}$ forms an inverse spinel structure with $Fe^{3+}$. $KNO_3$ may be added as the $Ni^{2+}$ oxidizing agent at an amount of 0.1 to 0.2 g per 1 mL of the mixed solution of nickel salt and iron salt.

Next, the mixed solution is subjected to a hydrothermal synthesis method to form a nanoparticle composite. In this case, maintaining a reaction temperature of 200° C. or higher and a reaction time of 8 hours or more is desirable to form an inverse spinel structure.

The method of the present invention may further include washing the reacted nanoparticle composite with at least one washing solvent selected from the group consisting of ethanol, acetone and water, and drying the nanoparticle composite in a temperature condition ranging from room temperature to 70° C.

Also, the present invention provides a nickel ferrite nanoparticle composite formed by hydrothermal synthesis of a polyol process, in which $Ni^{2+}$ and $Fe^{3+}$ form an inverse spinel structure. The nickel ferrite nanoparticles synthesized in the present invention show strong magnetism and simultaneously exist in the form of $Ni^{2+}$ in which Ni binds to a specific protein, thereby preventing loss of separability caused by additional oxidation and repeated recycling of the nanoparticles.

The nickel ferrite nanoparticle composite according to the present invention may have a magnetic saturation value of 40 to 50 emu/g.

In the nickel ferrite nanoparticle composite according to the present invention, a plurality of nickel ferrite nanoparticles are coagulated to form a nanoparticle cluster. In this case, the nickel ferrite nanoparticles may have a particle size of 7 to 10 nm, and the nickel ferrite nanoparticle composite particle may have a particle size of 80 to 200 nm.

Also, the present invention provides a protein binder which includes the nickel ferrite nanoparticle composite, and has properties of selectively binding to a protein comprising an amino acid selected from the group consisting of histidine, asparagine, arginine, cystine, glutamine, lysine, methionine, proline, and tryptophan. In this case, the protein binder is characterized in that it may be recycled.

Further, the present invention provides a method for selectively binding, separating or purifying a specific protein. Here, the method includes (1) allowing a protein binder comprising the nickel ferrite nanoparticle composite to bind to a specific protein included in a biological mixture, (2) separating the specific protein bound to the protein binder from the biological mixture using a magnetic field applied from the outside, and (3) separating the separated specific protein from the nickel ferrite nanoparticle composite. In this case, the protein may be a protein including at least one amino acid selected from the group consisting of histidine, asparagine, arginine, cystine, glutamine, lysine, methionine, proline, and tryptophan.

Hereinafter, preferred exemplary embodiments of the present invention will be described in order to aid in understanding the present invention. However, it should be understood that the description set forth herein is merely exemplary and illustrative of exemplary embodiments for the purpose of describing the present invention, and is not intended to limit the present invention.

EXAMPLES

Example 1: Synthesis of $NiFe_2O_4$ Nanoparticle Composite 0.36 g (1.5 mmol) of a nickel precursor compound, $NiCl_2$ (Aldrich, USA), and 0.81 g (3.0 mmol) of an iron precursor compound, $FeCl_3$ (Aldrich, USA), were added to 30 ml of a polyol solvent of ethylene glycol, and dissolved while agitating. 2.16 g of sodium acetate was added as a precipitating agent, and thoroughly agitated for 10 minutes. The resulting mixture was kept for 30 minutes, and agitated while adding an aqueous potassium nitrate solution obtained by dissolving 0.30 g of potassium nitrate in distilled water.

The resulting solution was put into a Teflon autoclave, and heated at a temperature of 200° C. for 8 hours. Thereafter, the solution was cooled to 25° C. in a thermostat to obtain a nanoparticle composite. To remove the polyol solvent of ethylene glycol from the obtained nanoparticle composite, the nanoparticle composite was washed several times with ethanol, and then dried at 60° C. for 10 hours.

Comparative Example 1

A nanoparticle composite was obtained in the same manner as in Example 1, except that the aqueous potassium nitrate solution was not added.

EXPERIMENTAL EXAMPLES

Experimental Example 1: Analysis of Structure of Magnetic Nanocomposite

To compare the structures of the magnetic nanocomposites prepared in Example 1 and Comparative Example 1, the magnetic nanocomposites were measured using XRD. The XRD measurement results are shown in FIG. 1.

As shown in FIG. 1, it could be seen that Ni was oxidized into $Ni^{2+}$, which then formed an inverse spinel structure in the case of Example 1 of the present invention in which the Ni oxidizing agent, $KNO_3$, was added, but in the case of Comparative Example 1 in which the Ni oxidizing agent, $KNO_3$ was not added, Ni was not oxidized but present in the form of a metal, and thus characteristic peaks of the Ni metal phase were observed. From these facts, it was confirmed that $KNO_3$ added as the Ni oxidizing agent had an influence on formation of the structure of the magnetic nanocomposite.

The SEM and TEM analysis results of the magnetic nanocomposite prepared in Example 1 are shown in FIGS. 2 and 3. As shown in FIG. 2, it could be seen that the magnetic nanocomposite had a diameter of 100 nm, as observed in the SEM image. As shown in FIG. 3, it could be seen that the magnetic nanocomposite was formed by coagulation of individual magnetic nanoparticles, and the individual magnetic nanoparticles had a diameter of 8 to 9 nm, as observed in the TEM image.

Experimental Example 2: Measurement of Chemical Binding Structure Using X-Ray Photoelectron Spectroscopy (XPS)

The spectra of a target metal oxide according to binding energy were measured using X-ray photoelectron spectroscopy (XPS). The measurement results are shown in FIG. 4. As shown in FIG. 4, it could be seen that the binding energy of Ni $2p_{3/2}$ was shifted to 855.8 eV, which was higher than the binding energy (852.6 eV) of $Ni^0$ known in the related art, as observed in the Ni 2p spectrum, and thus Ni was maintained in the state of $Ni^{2+}$.

Experimental Example 3: Analysis of Surface Structure of Magnetic Nanocomposite

A pore size distribution curve obtained from the analysis of adsorption results of the magnetic nanocomposite according to one exemplary embodiment of the present invention using a Barett-Joyner-Halenda (BJH) method is shown in FIG. 5.

As shown in FIG. 5, it could be seen that the magnetic nanocomposite according to one exemplary embodiment of the present invention included pores having various sizes spanning from nanosized micropores and small mesopores, which were formed by binding of the nanoparticles, to pores having a size of 100 nm, which were formed by coagulation of the nanoparticle composite. The Brunauer-Emmett-Teller (BET) surface area and the total pore volume of the nanoparticle composite were measured to be 105.0 $m^2/g$ and 0.27 $cm^3/g$, respectively, and thus the magnetic nanocomposite according to the present invention had a large surface area for adsorption of large amount of specific proteins.

Experimental Example 4: Analysis of Magnetic Behavior of Magnetic Nanocomposite

The magnetic behaviors of the magnetic nanocomposite were investigated using a superconducting quantum interference device (SQUID). The results are shown in FIG. 6. Referring to the magnetic hysteresis loop at 300 K, the magnetic nanocomposite had a high magnetic saturation value of 41.3 emu/g, the value of which was suitable for repetitive magnetic separation, was weakly superparamagnetic behavior, and showed low coercivity. The magnetic nanocomposite was able to be easily separated from the aqueous solution using a permanent magnet, and easily re-dispersed in water by vortexing or sonication.

Experimental Example 5: Analysis of Protein Separability of Magnetic Nanocomposite To determine the protein separability of the magnetic nanocomposite prepared in Example of the present invention, the magnetic nanocomposite was mixed with a His-tagged green fluorescent protein (GFP), and then allowed to bind to the His-tagged GFP.

The magnetic nanoparticle composite to which the protein was bound was separated from the solution using a magnet, and the separated magnetic nanoparticles were dispersed again in an aqueous imidazole solution (0.1 g/ml, 250 μl), and agitated for 30 minutes to separate proteins attached to the surface of the magnetic nanoparticle composite.

The magnetic nanoparticle composite was separated and removed again by applying a magnet so that the His-tagged GFP (30 μg/ml, 250 μl) separated from the nanoparticles was present in the solution. In each operation of the method, the fluorescence spectra of the GFP were measured to determine a separation level.

FIG. 7 shows the results obtained by measuring separability of a His-tagged GFP according to an amount of the added GFP. As shown in FIG. 7, it could be seen that 500 μg of the magnetic nanoparticle composite bound to 55 μg of the His-tagged GFP.

FIGS. 8 to 10 show levels of separation of the His-tagged GFP according to an amount and a reaction time of imidazole used, and show the results obtained by measuring a level of separation of imidazole according to the number of reactions with imidazole. As shown in FIGS. 8 to 10, it could be seen that at least 60% of the His-tagged protein bound to the magnetic nanoparticle composite according to one exemplary embodiment of the present invention was separated by the first reaction with imidazole. Also, it could be seen that the His-tagged GFP present in the initial solution bound to the nanoparticles, and approximately 60% of the His-tagged GFP was recovered by the aqueous imidazole solution.

The His-tagged GFP bound to the magnetic nanoparticle composite according to one exemplary embodiment of the present invention was not separated during a simple washing process, but the His-tagged GFP bound to the magnetic nanoparticle composite of Comparative Example 1 synthesized without using $KNO_3$ was easily separated during the simple washing process. This indicated that $Ni^{2+}$ and the histidine protein were bound to each other by means of ionic binding affinity in the case of the magnetic nanoparticle composite according to the present invention.

Experimental Example 6: Analysis of Selective Protein Separability of Magnetic Nanocomposite To analyze whether the magnetic nanoparticle composite according to one exemplary embodiment of the present invention selectively bound to histidine, the His-tagged GFP was mixed with an *E. coli* cell lysate, and reacted with the magnetic nanoparticle composite according to one exemplary embodiment of the present invention. Thereafter, the magnetic nanoparticle composite to which the proteins were bound was separated from the solution using a magnet, as described in Experimental Example 5. Then, the separated nanoparticles were dispersed again in an aqueous imidazole solution (0.1 g/ml, 250 μl), and agitated for 30 minutes to separate the proteins bound to the surface of the magnetic nanoparticle composite, and the separated proteins were confirmed by an SDS-PAGE analysis. The results are shown in FIG. 11.

As shown in FIG. 11, it could be seen that the magnetic nanoparticle composite according to one exemplary embodiment of the present invention selectively bound to the His-tagged GFP.

Experimental Example 7: Analysis of Recyclability of Magnetic Nanocomposite

To analyze whether the magnetic nanoparticle composite according to one exemplary embodiment of the present invention was recyclable after separation of proteins, the magnetic nanoparticle composite used in Experimental Example 6 was separated from the solution using a magnet, thermal treatment at 350° C. for 10 minutes, and then subjected to a protein separation experiment as described above in Experimental Example 6. The separation efficiencies according to the number of protein separation experiments are shown in FIGS. 12 and 13.

As shown in FIGS. 12 and 13, it could be seen that the magnetic nanoparticle composite according to one exemplary embodiment of the present invention had the 100% same bindability and separability when the magnetic nanoparticle composite was recycled up to 7 times, compared to those obtained when the magnetic nanoparticle composite was used for the first time.

The present invention has been described in detail. However, it should be understood that the detailed description and specific examples, while indicating preferred embodiments of the invention, are given by way of illustration only, since various changes and modifications within the scope of the invention will become apparent to those skilled in the art from this detailed description.

INDUSTRIAL APPLICABILITY

The method for preparing a magnetic nanoparticle composite according to the present invention includes a one-step hydrothermal synthesis method, and thereby the magnetic nanoparticle composite can be prepared in a simple and economic manner. Also, the nickel ferrite nanoparticles synthesized by the method of the present invention can be strongly magnetic, and also exist in the form of $Ni^{2+}$ in which Ni binds to a specific protein, thereby preventing loss of separability caused by additional oxidation and repeated recycling of the nanoparticles.

The invention claimed is:

1. A method for preparing a nickel ferrite nanoparticle composite having an inverse spinel structure, comprising:
    (1) preparing a mixed solution in which a nickel precursor compound id an iron precursor compound are mixed with a polyol solvent;
    (2) adding a pH control agent;
    (3) adding a $Ni^{2+}$ oxidizing agent and agitating the resulting mixed solution; and
    (4) heating the resulting mixed solution to form a nanoparticle composite through reduction of a nickel salt and an iron salt
    wherein
        said nickel precursor compound is $NiCl_2$,
        said iron precursor compound is $FeCl_3$,
        said pH control agent is sodium acetate,
        said polyol solvent is ethylene glycol (EG), and
        said $Ni^{2+}$ oxidizing agent is $KNO_3$, and
    wherein said nickel ferrite nanoparticle composite has a magnetic saturation value of 40 to 50 emu/g.

2. The method of claim 1, wherein a time required to maintain a reaction temperature of 200° C. or higher is greater than or equal to 8 hours in the heating of the resulting mixed solution to form the nanoparticle composite.

3. The method of claim 1, further comprising:
    washing the reacted nanoparticle composite with a washing solvent and drying the nanoparticle composite in a temperature condition ranging from room temperature to 70° C.

4. The method of claim 3, wherein the washing solvent is at least one selected from the group consisting of ethanol, acetone, and water.

* * * * *